United States Patent

Matsumoto et al.

[11] Patent Number: 6,010,689
[45] Date of Patent: Jan. 4, 2000

[54] HAIR TREATMENT COMPOSITIONS CONTAINING AMIDOPOLYETHER FUNCTIONAL SILICONE

[75] Inventors: Kyoko Matsumoto, Haga-cho; Tadashi Numata, Farnborough, both of Japan

[73] Assignee: Helene Curtis, Inc., Chicago, Ill.

[21] Appl. No.: 09/061,377

[22] Filed: Apr. 16, 1998

[30] Foreign Application Priority Data

Apr. 21, 1997 [GB] United Kingdom ............... 9707987

[51] Int. Cl.⁷ .................. A61K 7/11; A61K 7/06
[52] U.S. Cl. ............... 424/70.1; 424/47; 424/70.12; 514/579
[58] Field of Search ............ 424/47, 70.1, 70.12; 514/579

[56] References Cited

U.S. PATENT DOCUMENTS

| | | | |
|---|---|---|---|
| 3,958,581 | 5/1976 | Abegg et al. | 424/47 |
| 3,962,418 | 6/1976 | Birkofer | 424/70 |
| 4,009,256 | 2/1977 | Nowak, Jr. et al. | 424/70 |
| 5,194,251 | 3/1993 | Halloran et al. | 424/70 |
| 5,244,598 | 9/1993 | Merrifield et al. | 252/314 |

FOREIGN PATENT DOCUMENTS

| | | |
|---|---|---|
| 398 177 | 11/1990 | European Pat. Off. . |
| 612 514 | 8/1994 | European Pat. Off. . |
| 95/22311 | 8/1995 | WIPO . |

*Primary Examiner*—Thurman K. Page
*Assistant Examiner*—Lakshmi Channavajjala
*Attorney, Agent, or Firm*—Mathew Boxer

[57] ABSTRACT

A hair treatment composition for topical application comprising a hair treatment agent, and an amidopolyether functional silicone of general formula (I);

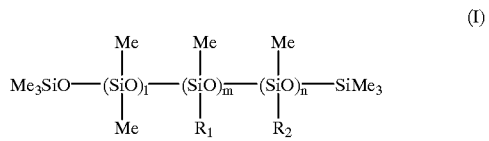

wherein $R1=(CH_2)_3-(NH-(CH_2)_2)_z-NH_2$, and
$R2=(CH_2)_3-(NH-(CH_2)_2)_z-NH-CO-CH_2-O-EO_x-(CH_2)_y-CH_3$
wherein l is in the region 100–1500, m is in the region 0–10, n is in the region 2–50, x is in the region 1–40, y is in the region 0–21, and z is in the region 0–1.

13 Claims, No Drawings

HAIR TREATMENT COMPOSITIONS CONTAINING AMIDOPOLYETHER FUNCTIONAL SILICONE

This invention relates to hair treatment compositions containing particular types of functional silicones, which can generate certain conditioning benefits whilst according the composition good physical properties.

The use of silicones as conditioning agents in hair treatment compositions is well known, and widely documented in the patent literature. However, a problem associated with such materials is that their use at levels necessary for achieving good tactile and/or visual benefits can make the hair too soft to style or retain a style. Fine hair in particular can appear limp and unmanageable.

In certain circumstances, there may also be a tendency for some silicones to cause the hair treatment composition in which they are included to discolour, in particular over a period of time. In particular, it is usual for manufacturers of shampoos to wish to sell their products not only in clear containers, but also in colours which may be for example delicate pastel colours, or white. Some silicones have been known to turn generally yellow on prolonged storage, thereby causing discoloration of the composition in which they are accommodated.

We have found that the addition of a certain species of amidopolyether functional silicone may impart to a hair treatment composition certain benefits in terms of conditioning, in particular in so called leave on compositions, where a wet smooth benefit may be observed. In addition, the incorporation of the amidofunctional polymer may also avoid some of the disadvantages associated with incorporating other silicones in hair treatment compositions, such as discoloration which may come about after prolonged storage.

Thus, according to a first aspect of the invention, there is provided a hair treatment composition for topical application comprising an amidopolyether functional silicone of general formula (I);

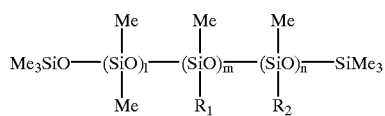

wherein R1=$(CH_2)_3$—$(NH$—$(CH_2)_2)_z$ —$NH_2$, and
R2=$(CH_2)_3$—$(NH$—$(CH_2)_2)_z$ —$NH$—$CO$—$CH_2$—$O$—$EO_x$—$(CH_2)_y$—$CH_3$ wherein 1 is in the region 100–500, m is in the region 0–10, n is in the region 2–50, x is in the region 1–40, y is in the region 0–21, and z is in the region 0–1. Preferably, 1+m is in the region 1–100.

Preferably, 1 may be in the region 200–600. Preferably, m may be in the region 0–5. Preferably, n may be in the region 10–30. Preferably, x may be in the region 2–10. Preferably, y may be in the region 5–20.

Suitable amidopolyether functional silicones for incorporating into hair treatment compositions according to the invention may readily be synthesised by those skilled in the art. They may be incorporated into water based hair treatment compositions by blending them with the other components of the composition during manufacture, in which case an emulsion will be formed in which the amidopolyether will be found in the hydrophobic phase of the composition.

The amidopolyether functional silicone is preferably present in the composition at a level of 0.01–50% by weight of the composition. Preferably, the amidopolyether functional silicone is present at a level of at least 0.05, more preferably at a level of at least 0.1% by weight of the composition. Preferably, the amidopolyether functional silicone is present at a level of less than 20% by weight, more preferably less than 10% by weight.

Hair treatment compositions according to the invention may suitably take the form of shampoos, conditioners, sprays, gels, mousses or lotions. Particularly preferred forms are shampoos, conditioners and especially mousses and gels.

(II) Shampoo Compositions

A preferred hair treatment composition in accordance with the invention is a shampoo composition.

Cleansing Surfactant

Such a shampoo composition will comprise one or more cleansing surfactants which are cosmetically acceptable and suitable for topical application to the hair.

The cleansing surfactant may suitably be selected from anionic, nonionic, amphoteric and zwitterionic surfactants, and mixtures thereof.

Examples of anionic surfactants are the alkyl sulphates, alkyl ether sulphates, alkaryl sulphonates, alkanoyl isethionates, alkyl succinates, alkyl sulphosuccinates, N-alkyl sarcosinates, alkyl phosphates, alkyl ether phosphates, alkyl ether carboxylates, and alpha-olefin sulphonates, especially their sodium, magnesium, ammonium and mono-, di- and triethanolamine salts. The alkyl and acyl groups generally contain from 8 to 18 carbon atoms and may be unsaturated. The alkyl ether sulphates, alkyl ether phosphates and alkyl ether carboxylates may contain from 1 to 10 ethylene oxide or propylene oxide units per molecule.

Typical anionic surfactants for use in shampoos of the invention include sodium oleyl succinate, ammonium lauryl sulphosuccinate, ammonium lauryl sulphate, sodium dodecylbenzene sulphonate, triethanolamine dodecylbenzene sulphonate, sodium cocoyl isethionate, sodium lauryl isethionate and sodium N-lauryl sarcosinate. The most preferred anionic surfactants are sodium lauryl sulphate, triethanolamine monolauryl phosphate, sodium lauryl ether sulphate 1 EO, 2EO and 3EO, ammonium lauryl sulphate and ammonium lauryl ether sulphate 1EO, 2EO and 3EO.

Examples of amphoteric and zwitterionic surfactants include alkyl amine oxides, alkyl betaines, alkyl amidopropyl betaines, alkyl sulphobetaines (sultaines), alkyl glycinates, alkyl carboxyglycinates, alkyl amphopropionates, alkylamphoglycinates, alkyl amidopropyl hydroxysultaines, acyl taurates and acyl glutamates, wherein the alkyl and acyl groups have from 8 to 19 carbon atoms. Typical amphoteric and zwitterionic surfactants for use in shampoos of the invention include lauryl amine oxide, cocodimethyl sulphopropyl betaine and preferably lauryl betaine, cocamidopropyl betaine and sodium cocamphopropionate.

The shampoo composition can also include co-surfactants, to help impart aesthetic, physical or cleansing properties to the composition. A preferred example is a nonionic surfactant, which can be included in an amount ranging from 0% to about 5% by weight based on total weight.

For example, representative nonionic surfactants that can be included in shampoo compositions of the invention include condensation products of aliphatic ($C_8$–$C_{18}$) primary or secondary linear or branched chain alcohols or phenols with alkylene oxides, usually ethylene oxide and generally having from 6 to 30 ethylene oxide groups.

Other representative nonionics include mono- or di-alkyl alkanolamides. Examples include coco mono- or di-ethanolamide and coco mono-isopropanolamide.

Further nonionic surfactants which can be included in shampoo compositions of the invention are the alkyl polyglycosides (APGs). Typically, the APG is one which comprises an alkyl group connected (optionally via a bridging group) to a block of one or more glycosyl groups. Preferred APGs are defined by the following formula:

$$RO-(G)_n$$

wherein R is a branched or straight chain alkyl group which may be saturated or unsaturated and G is a saccharide group.

R may represent a mean alkyl chain length of from about $C_5$ to about $C_{20}$. Preferably R represents a mean alkyl chain length of from about $C_8$ to about $C_{12}$. Most preferably the value of R lies between about 9.5 and about 10.5. G may be selected from $C_5$ or $C_6$ monosaccharide residues, and is preferably a glucoside. G may be selected from the group comprising glucose, xylose, lactose, fructose, mannose and derivatives thereof Preferably G is glucose.

The degree of polymerisation, n, may have a value of from about 1 to about 10 or more. Preferably, the value of n lies in the range of from about 1.1 to about 2. Most preferably the value of n lies in the range of from about 1.3 to about 1.5.

Suitable alkyl polyglycosides for use in the invention are commercially available and include for example those materials identified as: Oramix NS10 ex Seppic; Plantaren 1200 and Plantaren 2000 ex Henkel.

The total amount of surfactant (including any co-surfactant, and/or any emulsifier for the silicone component) in shampoo compositions of the invention is generally from 0.1 to 50% by weight, preferably from 5 to 30%, more preferably from 10% to 25% by weight of the total shampoo composition.

Cationic Deposition Polymer

A cationic deposition polymer is a preferred ingredient in shampoo compositions of the invention, for enhancing conditioning performance of the shampoo. By "deposition polymer" is meant an agent which enhances deposition of the silicone component from the shampoo composition onto the intended site during use, i.e. the hair and/or the scalp.

The deposition polymer may be a homopolymer or be formed from two or more types of monomers. The molecular weight of the polymer will generally be between 5,000 and 10,000,000, typically at least 10,000 and preferably in the range 100,000 to about 2,000,000. The polymers will have cationic nitrogen containing groups such as quaternary ammonium or protonated amino groups, or a mixture thereof.

The cationic nitrogen-containing group will generally be present as a substituent on a fraction of the total monomer units of the deposition polymer. Thus when the polymer is not a homopolymer it can contain spacer non-cationic monomer units. Such polymers are described in the CTFA Cosmetic Ingredient Directory, 3rd edition. The ratio of the cationic to non-cationic monomer units is selected to give a polymer having a cationic charge density in the required range.

Suitable cationic deposition polymers include, for example, copolymers of vinyl monomers having cationic amine or quaternary ammonium functionalities with water soluble spacer monomers such as (meth)acrylamide, alkyl and dialkyl (meth)acrylamides, alkyl (meth)acrylate, vinyl caprolactone and vinyl pyrrolidine. The alkyl and dialkyl substituted monomers preferably have $C_1$–$C_7$ alkyl groups, more preferably $C_1$–$C_3$ alkyl groups. Other suitable spacers include vinyl esters, vinyl alcohol, maleic anhydride, propylene glycol and ethylene glycol.

The cationic amines can be primary, secondary or tertiary amines, depending upon the particular species and the pH of the composition. In general secondary and tertiary amines, especially tertiary, are preferred.

Amine substituted vinyl monomers and amines can be polymerized in the amine form and then converted to ammonium by quaternization.

The cationic deposition polymers can comprise mixtures of monomer units derived from amine- and/or quaternary ammonium-substituted monomer and/or compatible spacer monomers.

Suitable cationic deposition polymers include, for example:

copolymers of 1-vinyl-2-pyrrolidine and 1-vinyl-3-methyl-imidazolium salt (e.g. chloride salt), referred to in the industry by the Cosmetic, Toiletry, and Fragrance Association, (CTFA) as Polyquaternium-16. This material is commercially available from BASF Wyandotte Corp. (Parsippany, N.J., USA) under the LUVIQUAT tradename (e.g. LUVIQUAT FC 370);

copolymers of 1-vinyl-2-pyrrolidine and dimethylaminoethyl methacrylate, referred to in the industry (CTFA) as Polyquaternium-11. This material is available commercially from Gaf Corporation (Wayne, N.J., USA) under the GAFQUAT tradename (e.g., GAFQUAT 755N);

cationic diallyl quaternary ammonium-containing polymers including, for example, dimethyldiallyammonium chloride homopolymer and copolymers of acrylamide and dimethyldiallylammonium chloride, referred to in the industry (CTFA) as Polyquaternium 6 and Polyquaternium 7, respectively;

mineral acid salts of amino-alkyl esters of homo-and co-polymers of unsaturated carboxylic acids having from 3 to 5 carbon atoms, (as described in U.S. Pat. No. 4,009,256);

cationic polyacrylamides(as described in WO95/22311).

Other cationic deposition polymers that can be used include cationic polysaccharide polymers, such as cationic cellulose derivatives, cationic starch derivatives, and cationic guar gum derivatives.

Cationic polysaccharide polymers suitable for use in compositions of the invention include those of the formula:

$$A-O-[R-N^+(R^1)(R^2)(R^3)X^-],$$

wherein: A is an anhydroglucose residual group, such as a starch or cellulose anhydroglucose residual. R is an alkylene, oxyalkylene, polyoxyalkylene, or hydroxyalkylene group, or combination thereof. $R^1$, $R^2$ and $R^3$ independently represent alkyl, aryl, alkylaryl, arylalkyl, alkoxyalkyl, or alkoxyaryl groups, each group containing up to about 18 carbon atoms. The total number of carbon atoms for each cationic moiety (i.e., the sum of carbon atoms in $R^1$, $R^2$ and $R^3$) is preferably about 20 or less, and X is an anionic counterion.

Cationic cellulose is available from Amerchol Corp. (Edison, N.J., USA) in their Polymer JR (trade mark) and LR (trade mark) series of polymers, as salts of hydroxyethyl cellulose reacted with trimethyl ammonium substituted epoxide, referred to in the industry (CTFA) as Polyquaternium 10. Another type of cationic cellulose includes the polymeric quaternary ammonium salts of hydroxyethyl cellulose reacted with lauryl dimethyl ammonium-substituted epoxide, referred to in the industry (CTFA) as Polyquaternium 24. These materials are available from Amerchol Corp. (Edison, N.J., USA) under the tradename Polymer LM-200.

Other suitable cationic polysaccharide polymers include quaternary nitrogen-containing cellulose ethers (e.g. as described in U.S. Pat. No. 3,962,418), and copolymers of etherified cellulose and starch (e.g. as described in U.S. Pat. No. 3,958,581).

A particularly suitable type of cationic polysaccharide polymer that can be used is a cationic guar gum derivative, such as guar hydroxypropyltrimonium chloride (Commercially available from Rhone-Poulenc in their JAGUAR trademark series)

Examples are JAGUAR C13S, which has a low degree of substitution of the cationic groups and high viscosity. JAGUAR C15, having a moderate degree of substitution and a low viscosity, JAGUAR C17 (high degree of substitution, high viscosity), JAGUAR C16, which is a hydroxypropylated cationic guar derivative containing a low level of substituent groups as well as cationic quaternary ammonium groups, and JAGUAR 162 which is a high transparency, medium viscosity guar having a low degree of substitution.

Preferably the cationic deposition polymer is selected from cationic cellulose and cationic guar derivatives. Particularly preferred deposition polymers are JAGUAR C13S, JAGUAR C15, JAGUAR C17 and JAGUAR C16 and JAGUAR C162.

(III) Conditioners

Compositions in accordance with the invention may also be formulated as conditioners for the treatment of hair (typically after shampooing) and subsequent rinsing.

Conditioning Surfactant

Such a conditioner will comprise one or more conditioning surfactants which are cosmetically acceptable and suitable for topical application to the hair. Suitable conditioning surfactants are selected from cationic surfactants, used singly or in admixture. Examples include quaternary ammonium hydroxides or salts thereof, e.g chlorides.

Suitable cationic surfactants for use in hair conditioners of the invention include cetyltrimethylammonium chloride, behenyltrimethylammonium chloride, cetylpyridinium chloride, tetramethylammonium chloride, tetraethylammonium chloride, octyltrimethylammonium chloride, dodecyltrimethylammonium chloride, hexadecyltrimethylammonium chloride, octyldimethylbenzylammonium chloride, decyldimethylbenzylammonium chloride, stearyldimethylbenzylammonium chloride, didodecyldimethylammonium chloride, dioctadecyldimethylammonium chloride, tallow trimethylammonium chloride, cocotrimethylammonium chloride, and the corresponding hydroxides thereof.

Further suitable cationic surfactants include those materials having the CTFA designations Quaternium-5, Quaternium-31 and Quaternium-18.

Further suitable cationic surfactants include acid-neutralised amidoamine compounds, wherein the amidoamine compound has the general structural formula (I):

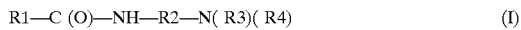

R1—C(O)—NH—R2—N(R3)(R4)    (I)

wherein R1 is a fatty acid chain containing from 12 to 22 carbon atoms, R2 is an alkylene group containing from one to four carbon atoms, and R3 and R4 are, independently, an alkyl group having from one to four carbon atoms.

Examples of suitable amidoamine compounds of general structural formula (I) include stearamidopropyl dimethylamine, stearamidopropyl diethylamine, stearamidoethyl dimethylamine, stearamidoethyl diethylamine, palmitamidopropyl dimethylamine, behenamidopropyl dimethylamine, myristamidopropyl dimethylamine, oleamidopropyl dimethylamine, ricinoleamidopropyl dimethylamine, and combinations thereof.

The acid used to neutralise the amidoamine compound can be essentially any organic acid or mineral acid of sufficient acid strength to neutralise a free amine nitrogen. Such acids include hydrochloric acid, sulphuric acid, nitric acid, phosphoric acid, lactic acid, citric acid, tartaric acid, acetic acid, gluconic acid, glycolic acid and propionic acid, or combinations thereof.

In general, a sufficient amount of acid is added to neutralise the amidoamine compound and to adjust the final pH of the composition to within a range of from about 2.5 to about 6, preferably in a pH range of from about 3 to about 5.

Mixtures of any of the foregoing materials may also be suitable. Particularly useful cationic surfactants for use in hair conditioners of the invention include cetyltrimethylammonium chloride, (available commercially, for example as GENAMIN CTAC, ex Hoechst Celanese), and stearamidopropyldimethylamine, preferably neutralised with lactic acid.

In conditioners of the invention, the level of cationic surfactant is preferably from 0.01 to 10%, more preferably 0.05 to 5%, most preferably 0.1 to 2% by weight of the composition.

Fatty Alcohol

Conditioners of the invention advantageously incorporate a fatty alcohol material. The combined use of fatty alcohol materials and cationic surfactants in conditioning compositions is believed to be especially advantageous, because this leads to the formation of a lamellar phase, in which the cationic surfactant is dispersed.

Representative fatty alcohols comprise from 8 to 22 carbon atoms, more preferably 16 to 20. Examples of suitable fatty alcohols include cetyl alcohol, stearyl alcohol and mixtures thereof. The use of these materials is also advantageous in that they contribute to the overall conditioning properties of compositions of the invention.

The level of fatty alcohol material in conditioners of the invention is conveniently from 0.01 to 10%, preferably from 0.1 to 5% by weight of the composition. The weight ratio of cationic surfactant to fatty alcohol is suitably from 10:1 to 1:10, preferably from 4:1 to 1:8, optimally from 1:1 to 1:4.

(IV) Mousses

Hair treatment compositions in accordance with the invention may also take the form of aerosol foams (mousses) in which case a propellant must be included in the composition. This agent is responsible for expelling the other materials from the container and forming the hair mousse character.

The propellant gas can be any liquefiable gas conventionally used for aerosol containers. Examples of suitable propellants include dimethyl ether, propane, n-butane and isobutane, used singly or in admixture.

The amount of the propellant gases is governed by normal factors well known in the aerosol art. For hair mousses, the level of propellant is generally from about 3% to about 30%, preferably from about 5% to about 15% of the total composition.

Small quantities of surfactant ranging anywhere from 0.1 to about 10%, preferably from about 0.1 to about 1%, most preferably about 0.3% by weight may be present in the hair mousse compositions of the invention. The surfactant may be an anionic, nonionic or cationic emulsifier. Particularly preferred are nonionic emulsifiers which are formed from alkoxylation of hydrophobes such as fatty alcohols, fatty acids and phenols.

(V) Hair Styling Gels

Hair treatment compositions in accordance with the invention may also take the form of leave on hair styling gels.

Such a hair styling gel will normally contain about 0.01% to about 3%, preferably 0.1% to 2%, most preferably from 0.2% to 1.5%, by weight of the composition, of a viscosity enhancer.

The viscosity enhancer can be a gelling agent or a thickener, or any other compound capable of imparting a suitable gel-type viscosity to the composition.

A suitable viscosity for a hair styling gel of the invention is about 10,000 up to about 100,000, preferably 20,000 to 100,000, most preferably 30,000 to 90,000 centipoise (as measured on a Brookfield Viscometer with a #6 spindle at 5 rpm). Lower viscosities, however, may be preferable if liquid gel- type formulations are desired.

Examples of viscosity enhancers include:

cellulose derivatives such as methylcellulose, hydroxymethylcellulose, hydroxyethyl cellulose, hydroxypropylcellulose, and hydroxypropyl methylcellulose;

water-soluble salts of cellulose ethers such as sodium carboxymethyl cellulose and sodium carboxymethyl hydroxyethyl cellulose;

natural gums such as carrageenan, xanthan gum, gum arabic, gum tragacanth and guar gum and derivatives thereof such as hydroxypropyl guar and guar hydroxypropyl trimonium chloride;

inorganic thickeners such as colloidal magnesium aluminium silicate (Veegum), finely divided silica, natural clays such as bentonite and synthetic clays such as the synthetic hectorite available as Laponite(ex Laporte Industries Ltd);

vinyl-type polymeric thickeners such as polyvinylpyrrolidone, polyvinyl alcohol, sodium acrylate/vinyl alcohol copolymers and carboxyvinyl polymers, such as those polymers of acrylic acid cross-linked with about 0.75% to 2.0% of polyallylsucrose or polyallylpentaerythritol, obtainable under the Carbopol trademark from B.F.Goodrich.

Small quantities of surfactant ranging anywhere from 0.1 to about 10%, preferably from about 0.1 to about 1%, most preferably about 0.5% by weight may be present in hair styling gels of the invention. The surfactant may be an anionic, nonionic or cationic emulsifier. Particularly preferred are nonionic emulsifiers which are formed from alkoxylation of hydrophobes such as fatty alcohols, fatty acids and phenols.

(VI) Optional Ingredients

Compositions of this invention may contain any other ingredient normally used in hair treatment formulations. These other ingredients may include viscosity modifiers, preservatives, colouring agents, polyols such as glycerine and polypropylene glycol, chelating agents such as EDTA, antioxidants, fragrances, antimicrobials and sunscreens. Each of these ingredients will be present in an amount effective to accomplish its purpose. Generally these optional ingredients are included individually at a level of up to about 5% by weight of the total composition.

Preferably, compositions of this invention also contain adjuvants suitable for hair care. Generally such ingredients are included individually at a level of up to 2%, preferably up to 1%, by weight of the total composition.

Among suitable hair care adjuvants, are:

(i) natural hair root nutrients, such as amino acids and sugars. Examples of suitable amino acids include arginine, cysteine, glutamine, glutamic acid, isoleucine, leucine, methionine, serine and valine, and/or precursors and derivatives thereof. The amino acids may be added singly, in mixtures, or in the form of peptides, e.g. di- and tripeptides. The amino acids may also be added in the form of a protein hydrolysate, such as a keratin or collagen hydrolysate. Suitable sugars are glucose, dextrose and fructose These may be added singly or in the form of, e.g. fruit extracts. A particularly preferred combination of natural hair root nutrients for inclusion in compositions of the invention is isoleucine and glucose. A particularly preferred amino acid nutrient is arginine.

(ii) hair fibre benefit agents. Examples are:

ceramides, for moisturising the fibre and maintaining cuticle integrity. Ceramides are available by extraction from natural sources, or as synthetic ceramides and pseudoceramides. A preferred ceramide is Ceramide II, ex Quest. Mixtures of ceramides may also be suitable, such as Ceramides LS, ex Laboratoires Serobiologiques.

Mode of Use

The compositions of the invention are primarily intended for topical application to the hair and/or scalp of a human subject to improve hair fibre surface properties such as smoothness, softness, manageability, cuticle integrity, and shine.

The invention is further illustrated by way of the following non-limitative examples:

EXAMPLES

Example 1

The conditioning effect of amidopolyether functional silicones according to the invention was evaluated.

A team of trained panellists evaluated 100 g hair tresses treated with 1 ml of a solution of a test silicone dissolved in volatile paraffin. The solvent was evaporated and the switch was re-wet with water, and panellists were asked to compare the wet smoothness of the amidopolyether (J68) against dimethicone fluid DC200 (60,000cs), and give each a score from +2 (good wet smoothness) to −2 (poor wet smoothness). The results showed that the amidopolyether had a superior wet smoothness (0.72 vs. −0.33) compared to the dimethicone.

Example 2

A leave on styling gel formulation was prepared containing an amidopolyether functional silicone according to the invention, which was tested against a control formulation.

| Ingredient | Control (%) | Test (%) |
| --- | --- | --- |
| Carbopol 980 | 0.3 | 0.3 |
| Dimethicone copolyol | 1.0 | 1.0 |
| POP(9) diglyceryl ether | 3.3 | 3.3 |
| Ethanol | 20.0 | 20.0 |
| Amidopolyether | — | 3.0 |
| POE(20) Sorbitan monolaurate | 0.5 | 0.5 |
| Minor ingredients | qs | qs |
| Water | to 100 | to 100 |

An amount of gel was applied to a standard hair switch. 10.0 g of hair in the form of a switch was worked in 1.0 g of a non-conditioning shampoo, lathered for 30 seconds, and rinsed with water. The switches were then washed with 1 g of conditioner for 1 minute, and rinsed with water. The procedure was repeated once. Three switches of hair were prepared for each product evaluated. The evaluation was carried out by twelve trained panellists as a paired comparison test and significant differences at greater than 95% confidence were assessed. For wet smoothness evaluations, the hair was kept damp between evaluations by spraying with water. The smoothness of each switch was assessed by the experts using their non-writing hand.

Switches were tested for smoothness of feel and dry combing properties; 82% of the evaluating panel (p<0.05) expressed a preference for the dry smoothness of the test composition verses the control, and 86% (p<0.05) expressed a preference for the test composition verses the control for the dry combing properties.

Similar evaluation tests were conducted for conditioner formulations which were prepared according to the compositions below;

| Ingredient | Control (%) | Test (%) |
|---|---|---|
| Cetyl trimethyl ammonium chloride | 0.7 | 0.7 |
| Stearyl alcohol | 2.2 | 2.2 |
| Cetyl palmitate | 0.5 | 0.5 |
| Paraffin wax | 1.0 | 1.0 |
| Paraben | 0.2 | 0.2 |
| Vitamin E acetate | 0.05 | 0.05 |
| Perfume | 0.4 | 0.4 |
| Amidopolyether | — | 3.0 |
| Water | to 100 | to 100 |

Switches were evaluated by a panel according to the protocol described above in terms of the dry smoothness of feel and wet smoothness. 57% (p<0.01) preferred the test composition to the control in terms of dry smoothness of feel, whereas 96% (p<0.001) preferred the test composition to the control with regard to its wet smoothness feel.

Example 3

A shampoo composition was prepared by mixing the following components in the amounts stated.

| Component | % by weight |
|---|---|
| Sodium lauryl ether sulphate 2EO | 16.0 |
| Cocamidopropyl betaine | 2.0 |
| Jaguar C13S | 0.2 |
| CARBOPOL 980 | 0.4 |
| Silicone[1] | 3.3 |
| Preservative colour, fragrance | q.s. |
| Water | to 100% |

[1]J68, an amidopolyether functional silicone, ex. Toray Silicone.

Example 4

A hair conditioning composition was prepared by mixing the following components in the amounts stated.

| Component | % by weight |
|---|---|
| Cetyl trimethylammonium chloride | 0.7 |
| Cetostearyl alcohol | 2.0 |
| Glyceryl monostearate | 0.7 |
| Paraffin wax | 1.0 |
| Silicone | 3.3 |

-continued

| Component | % by weight |
|---|---|
| Preservative, colour, fragrance | q.s. |
| Water | to 100% |

Example 5

A hair mousse was prepared by mixing the following components in the amounts stated.

| Component | % by weight |
|---|---|
| Silicone[1] | 1.0 |
| EMPILAN NP9[2] | 0.3 |
| Butane/propane | 5.5 |
| Preservative, fragrance | q.s. |
| Water | to 100 |

[2]Nonyl phenol ethoxylate 9EO, ex Albright & Wilson

The compositions of Examples 1–3 provided conditioning benefits to the hair.

We claim:

1. A hair treatment composition for topical application comprising an amidopolyether functional silicone of formula (I);

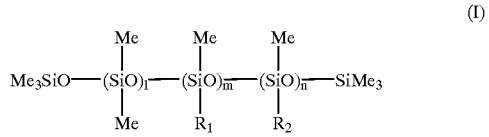

wherein R1=(CH$_2$)$_3$—(NH—(CH$_2$)$_2$)$_z$—NH$_2$, and

R2=(CH$_2$)$_3$—(NH—(CH$_2$)$_2$)$_z$—NH—CO—CH$_2$—O—EO$_x$—(CH$_2$)$_y$—CH$_3$ wherein 1 is in between 100–1500, m is in between 0–10, n is in between 2–50, x is in the between 1–40, y is in between 0–21, and z is in between 0–1.

2. A hair treatment composition according to claim 1, wherein 1+m are in between 1–100.

3. A hair treatment composition according to claim 1, wherein 1 is in between 200–600.

4. A hair treatment composition according to claim 1, wherein m is in the region 0–5.

5. A hair treatment composition according to claim 1, wherein n is in between 10–30.

6. A hair treatment composition according to claim 1, wherein x is in between 2–10.

7. A hair treatment composition according to claim 1, wherein y is in between 5–20.

8. A hair treatment composition according to claim 1, wherein the amidopolyether functional silicone is present in the composition at a level of 0.01–50% by weight of the composition.

9. A hair treatment composition according to claim 1, which is a conditioning composition containing one or more conditioning agents.

10. A hair treatment composition according to claim 1, comprising a deposition aid a fatty alcohol material.

11. A hair treatment composition according to claim 10, comprising from about 0.01 to about 5% by weight of a deposition aid which is a cationic polymer selected from the group comprising hydroxyalkyl cellulose ethers, cationic guar derivatives and cationic polyacrylamides.

12. A hair treatment composition according to claim 1, wherein the composition is a leave on composition.

13. A hair treatment composition according to claim 12, wherein the composition is a gel or mousse.

* * * * *